(12) United States Patent
Suzuki et al.

(10) Patent No.: US 10,478,537 B2
(45) Date of Patent: Nov. 19, 2019

(54) CELL SEPARATION FILTER MATERIAL AND FILTER OBTAINED BY LAYERING SAME

(71) Applicant: KANEKA CORPORATION, Kita-ku (JP)

(72) Inventors: Ikuhiro Suzuki, Takasago (JP); Takayuki Miyamoto, Takasago (JP); Takao Shibata, Takasago (JP)

(73) Assignee: KANEKA CORPORATION, Kita-ku (JP)

( * ) Notice: Subject to any disclaimer, the term of this patent is extended or adjusted under 35 U.S.C. 154(b) by 474 days.

(21) Appl. No.: 15/030,130

(22) PCT Filed: Oct. 7, 2014

(86) PCT No.: PCT/JP2014/076798
§ 371 (c)(1),
(2) Date: Apr. 18, 2016

(87) PCT Pub. No.: WO2015/056603
PCT Pub. Date: Apr. 23, 2015

(65) Prior Publication Data
US 2016/0263297 A1    Sep. 15, 2016

(30) Foreign Application Priority Data
Oct. 18, 2013   (JP) ................................. 2013-217672

(51) Int. Cl.
*A61M 1/02*       (2006.01)
*A61M 1/36*       (2006.01)
(Continued)

(52) U.S. Cl.
CPC ........ *A61M 1/0218* (2014.02); *A61M 1/3496* (2013.01); *A61M 1/3672* (2013.01); *B01D 39/1623* (2013.01)

(58) Field of Classification Search
CPC ........ B01D 39/1623; B01D 2239/1233; B01D 2239/1216; B01D 2239/1291;
(Continued)

(56) References Cited

U.S. PATENT DOCUMENTS 4,701,267 A    10/1987  Watanabe et al.
6,048,464 A     4/2000  Tanaka et al.
(Continued)

FOREIGN PATENT DOCUMENTS

CN        1176607 A     3/1998
CN      101053683 A    10/2007
(Continued)

OTHER PUBLICATIONS

International Search Report dated Jan. 20, 2015 in PCT/JP2014/076798, filed Oct. 7, 2014.
(Continued)

*Primary Examiner* — Krishnan S Menon
*Assistant Examiner* — Waqaas Ali
(74) *Attorney, Agent, or Firm* — Oblon, McClelland, Maier & Neustadt, L.L.P.

(57) ABSTRACT

An object of the present invention is to provide a novel filter material and a filter including the same. Specifically, the present invention aims to provide a filter material capable of filtering in a short period of time, without clogging of the filter, while maintaining high cell separation properties, and a filter including the same. More specifically, the present invention aims to provide a filter material in which fiber masses (flocs) are uniformly distributed, and a filter including the same. The present invention provides a novel filter material showing excellent cell separation properties and excellent flow-through properties regardless of design choices for filters known prior to the filing of the present
(Continued)

application, and an efficient cell separation method using a novel filter on which the filter material is stacked.

12 Claims, 1 Drawing Sheet

(51) Int. Cl.
    *A61M 1/34*     (2006.01)
    *B01D 39/16*     (2006.01)
    *A61M 1/38*     (2006.01)

(58) Field of Classification Search
    CPC .............. A61M 1/0218; A61M 1/3672; A61M 1/3496; A61M 1/38; A61M 1/3635; A61M 1/3633; A61M 2202/0028; A61M 2205/7527; A61M 2205/75; A61M 2202/0014
    See application file for complete search history.

(56) References Cited

U.S. PATENT DOCUMENTS

| | | | |
|---|---|---|---|
| 2006/0184085 A1* | 8/2006 | Kimura | A61M 1/3496 604/6.03 |
| 2008/0011691 A1 | 1/2008 | Yamada et al. | |
| 2008/0110829 A1 | 5/2008 | Kobayashi | |
| 2011/0031191 A1 | 2/2011 | Fukuda et al. | |
| 2013/0277297 A1 | 10/2013 | Suzuki et al. | |

FOREIGN PATENT DOCUMENTS

| | | |
|---|---|---|
| CN | 101098704 A | 1/2008 |
| CN | 100522308 C | 8/2009 |
| CN | 102006876 A | 4/2011 |
| JP | 63-175156 A | 7/1988 |
| JP | 2-203909 A | 8/1990 |
| JP | 9-155127 A | 6/1997 |
| JP | 11-94767 A | 4/1999 |
| JP | 2000-517240 A | 12/2000 |
| JP | 4134043 B2 | 8/2008 |
| JP | 2012-183237 A | 9/2012 |
| JP | 2012-183237 A | 9/2012 |
| JP | 2012183237 A * | 9/2012 |
| WO | WO 96/03194 A1 | 2/1996 |
| WO | 2004/050146 A1 | 6/2004 |
| WO | WO 2005/044418 A2 | 5/2005 |
| WO | 2005/120600 A1 | 12/2005 |
| WO | 2012/057029 A1 | 5/2012 |
| WO | WO 2012/102398 A1 | 8/2012 |

OTHER PUBLICATIONS

International Preliminary Report on Patentability and Written Opinion dated Apr. 19, 2016 in PCT/JP2014/076798, filed Oct. 7, 2014.

* cited by examiner

CELL SEPARATION FILTER MATERIAL AND FILTER OBTAINED BY LAYERING SAME

TECHNICAL FIELD

The present invention relates to a novel filter material for separating cells from a cell-containing liquid and a filter on which the filter material is stacked.

BACKGROUND ART

There are two methods for separating cells from cell-containing liquids such as blood: the centrifugation method which uses the difference in specific gravity of cells; and the filtration method in which a porous body is used as a filter material. The filtration method which offers high cell separation properties by a simple operation at low cost has been widely and commonly used. In the current market, there are needs for filters having higher cell separation properties. However, filters according to conventional techniques cannot easily achieve cell separation properties that are high enough to meet the market needs by simply increasing the amount of filter material. To solve this problem, various improvements have been reported in filters using nonwoven fabrics as filter materials. Examples include a method of decreasing average fiber diameter, a method of increasing packing density, a method of uniformizing fiber diameter distribution or pore size, a method of reducing variations in pore size distribution in a mixture of fibers of different thicknesses, and a method of uniformizing both fiber diameter and basis weight (Patent Literatures 1 to 4). However, if the above methods are actually tried to increase cell separation properties, the increase in cell separation properties will be accompanied by an increase in pressure loss in the filter portion during passage of cell-containing liquids, which unfortunately results in an extreme reduction in throughput rate before the completion of the filtration of a desired amount of cell-containing liquid to be treated.

Moreover, in addition to uniformization of a single property element such as, typically, fiber diameter or average pore size, studied have been made on the standard deviation of fiber density of the entire filter material, and a method of reducing the fiber density variation difference of the entire filter material, or in other words a filter material having a low formation index has been reported (Patent Literature 5). However, even filter materials having low formation indices may fail to provide sufficient cell separation properties due to flowing of the cell-containing liquid on one side. In addition, the concentrated flow of cell-containing liquid on a portion of the filter causes clogging, which unfortunately results in a longer treatment time.

As described above, although many filters for separating cells have been examined, the problems such as the reduction in throughput rate associated with the improvement of cell separation properties and clogging in filters have not yet been solved.

CITATION LIST

Patent Literature

Patent Literature 1: JP-A H02-203909
Patent Literature 2: JP-A S63-175156
Patent Literature 3: JP-A H09-155127
Patent Literature 4: WO 96/03194
Patent Literature 5: JP-B 4134043

SUMMARY OF INVENTION

Technical Problem

An object of the present invention is to provide a novel filter material that solves the above problems and a filter including the same. Specifically, the present invention aims to provide a filter material capable of filtering in a short period of time, without clogging of the filter, while maintaining high cell separation properties, and a filter including the same. More specifically, the present invention aims to provide a filter material in which masses (flocs) of fibers are uniformly distributed and a filter including the same.

Solution to Problem

As a result of extensive studies on the above problems, the present inventors have found that a novel filter material in which masses (flocs) of fibers are uniformly distributed can be used to prepare a cell separation filter having high cell separation properties and capable of filtering in a short period of time without clogging. The present invention has been made based on such findings.

Specifically, the present invention relates to a filter material, having an average fiber diameter of 0.3 to 5.0 μm, a thickness of 0.10 to 0.60 mm, and an average floc size index of 1.0 to 4.0.

The filter material preferably has a floc size index ratio of 0.78 to 1.02.

The filter material preferably has an average floc size index corresponding to that determined for a thickness of 0.30 mm of 1.0 to 3.0.

The filter material preferably has a floc size index ratio corresponding to that determined for a thickness of 0.30 mm of 0.84 to 1.02.

Preferably, the filter material contains a hydrophilic polymer on at least a surface thereof.

Preferably, the filter material is a nonwoven fabric.

The present invention also relates to a filter, provided with an inlet and an outlet for a liquid, the filter including at least one filter material having an average fiber diameter of 0.3 to 30 μm and a basis weight of 10 to 100 g/m$^2$, wherein at least one of the at least one filter material is a filter material having an average floc size index of 1.0 to 4.0.

In the filter, preferably, at least one of the at least one filter material is a filter material having a floc size index ratio of 0.78 to 1.02.

In the filter, preferably, at least one of the at least one filter material is a filter material having an average floc size index corresponding to that determined for a thickness of 0.30 mm of 1.0 to 3.0.

In the filter, preferably, at least one of the at least one filter material is a filter material having a floc size index ratio corresponding to that determined for a thickness of 0.30 mm of 0.84 to 1.02.

In the filter, preferably, the filter material is stacked in a liquid flow direction.

Preferably, the filter includes a different type of filter material on an inlet side and/or outlet side of the filter.

In the filter, preferably, a filter material having a large average fiber diameter is placed on an inlet side of the filter while a filter material having a small average fiber diameter is placed on an outlet side of the filter.

Preferably, the filter includes a pre-filter material for removing microscopic aggregates on an inlet side of the filter.

The present invention also relates to a filter system, including: the filter; a blood collection bag connected to an inlet side of the filter; and at least one blood bag connected to an outlet side of the filter.

Advantageous Effects of Invention

The present invention provides a novel filter material showing excellent cell separation properties and excellent flow-through properties regardless of design choices for filters known prior to the filing of the present application, and an efficient cell separation method using a novel filter on which the filter material is stacked.

DESCRIPTION OF EMBODIMENTS

The present invention is described in detail below. The filter material of the present invention is a filter material for selectively separating cells from a cell-containing liquid. It means a novel filter showing excellent cell separation properties and excellent flow-through properties regardless of design choices for filters known prior to the filing of the present application, and a novel filter on which the filter material is stacked. For example, it is a novel filter material showing excellent cell separation properties and excellent flow-through properties regardless of formation index.

The cell-containing liquid in the present invention is a generic term for body fluids or synthetic liquids containing cells, and liquid cell cultures. Examples include whole blood and liquids consisting of a single or multiple types of blood components prepared from whole blood, such as whole blood, red cell concentrates, washed red cell suspensions, frozen thawed red cell concentrates, blood for exchange transfusion, platelet-poor plasma (PPP), platelet-rich plasma (PRP), plasma, frozen plasma, platelet concentrates, and buffy coat (BC); solutions of these liquids containing additives such as anticoagulants or preservative solutions; whole blood preparations; red cell preparations; platelet preparations; plasma preparations; bone marrow fluid; cord blood; liquids obtained by treating body tissues; and solutions obtained by culturing cells such as ES cells, iPS cells, adult stem cells, or somatic cells.

In the present invention, a specific type of cells can be selectively separated bypassing the cell-containing liquid through the filter material. The type of cells to be selectively separated may be ES cells, iPS cells, adult stem cells (e.g. mesenchymal stem cells, hematopoietic stem cells), somatic cells (leukocytes, erythrocytes, platelets, monocytes, mononuclear cells, lymphocytes, epithelial cells, circulating tumor cells) or the like. In particular, leukocytes, platelets, hematopoietic stem cells, and circulating tumor cells are preferred among the above types of cells because these cells can be easily separated by the filter material of the present invention.

In the filter material of the present invention, the average floc size index which is an index indicating the size of mass (floc) of fibers and the floc size index ratio by which the orientation of the fibers is evaluated are in specific ranges.

Figure 1:
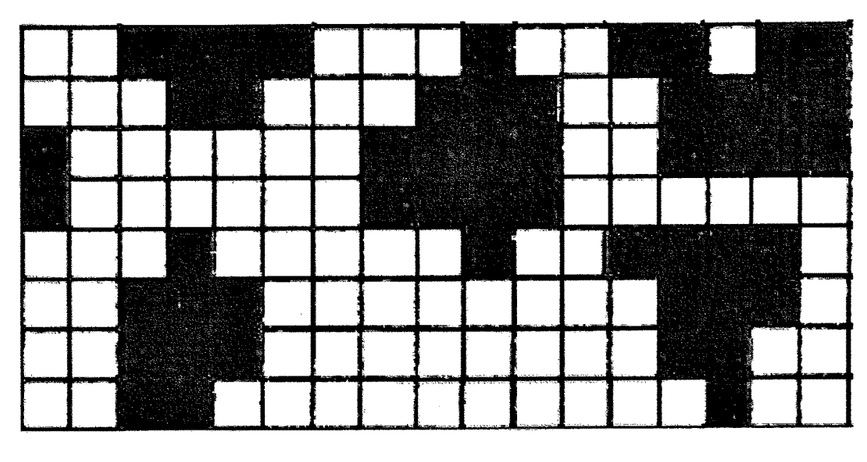
FIG. 1 shows a binary image produced from the absorbance of light transmitted through a filter material as detected by a charge-coupled device camera.

The term "average floc size index" as used herein refers to a value obtained by irradiating the filter material with light from below, detecting the light transmitted therethrough using a charge-coupled device camera (hereinafter abbreviated to "CCD camera"), producing a binary image as shown in FIG. 1 from the absorbance detected in each pixel of the CCD camera, scanning all the pixels in the binary image in the cross method (CD) and the machine direction (MD), and averaging the number of consecutive black dots. The average floc size index reveals the size and the distribution of mass (floc) of fibers in the filter material.

The term "floc size index ratio" as used herein refers to a value obtained by dividing the average floc size index in the cross direction by the average floc size index in the machine direction. The floc size index ratio reveals the orientation of the fibers in the filter material.

Specifically, calculation is carried out as follows using the following computational formulas (1) to (6).
(1) The transmittance of each pixel is determined using a CCD camera as follows:

Transmittance=((the amount of light when the light is on)−(the amount of light when the light is off))/((the amount of light when the light is on with no sample)−(the amount of light when the light is off with no sample))×100(%).

(2) The average transmittance (average of transmittances measured in all pixels) is determined.
(3) A binary image is produced by converting pixels having higher transmittances than the average transmittance into white dots and pixels having lower transmittances therethan into black dots.
(4) All the pixels in the binary image are scanned in the cross direction (CD) and the machine direction (MD) and the number of consecutive black dots is averaged to determine the average number in the cross direction, the average number in the machine direction, and the average number in both directions.
(5) The average floc size index is determined by the following formula:

(Average floc size index)=((average floc size index in the cross direction)+(average floc size index in the machine direction))/2.

(6) The ratio of the index in the cross direction to the index in the machine direction (aspect ratio) is determined by the following formula:

(Floc size index ratio)=(average floc size index in the cross direction)/(average floc size index in the machine direction).

The average floc size index and the floc size index ratio are measured using a formation tester, FMT-MIII (Nomura Shoji Co., Ltd.). Measurement is carried out without changing the factory default settings of the measurement device and with a total number of pixels of the CCD camera of about 3400. In the present invention, the average floc size index and the floc size index ratio are measured by adjusting the measurement size to 4.6 cm×4.6 cm (1 pixel size=0.79 mm×0.79 mm) so that the total number of pixels is about 3400, although the measurement size may be changed in accordance with the sample shape to provide the same total number of pixels.

In the present invention, the average floc size index and the floc size index ratio are calculated as follows. First, three filter materials that are identical in terms of the type of material, fiber diameter, packing ratio, and thickness are prepared, and the average floc size index and the floc size index ratio of each filter material are measured as described above. Subsequently, the average of the average floc size indices and the average of the floc size index ratios of the three filter materials are defined as the average floc size index and the floc size index ratio of the filter materials, respectively. When the necessary number of filter materials for the measurement cannot be obtained from a single filter, filter materials from identical filters may be combined and measured.

In the present invention, a higher average floc size index indicates a larger size of mass (floc) of fibers in the filter material, which means that the distribution of the fibers in the filter material is uneven. If a cell-containing liquid is flowed through such a filter material, the flow concentrates on portions having low fiber density and low blood flow-through resistance, while portions having high fiber density and high blood flow-through resistance are not sufficiently utilized. Therefore, the cell separation properties of the filter are reduced as the entire surface of the filter material is not effectively used. Further, the concentrated flow of cell-containing liquid on a portion of the filter causes clogging, thereby reducing the flow-through rate of the filter. On the other hand, a lower average floc size index indicates a smaller size of mass (floc) of fibers in the filter material, which means that the fibers of the filter material are uniformly distributed. If a cell-containing liquid is flowed through such a filter material, the cell-containing liquid flows uniformly through the filter material. Therefore, the cell separation properties of the filter are increased as the entire surface of the filter material is effectively used. Further, the flow of cell-containing liquid spreads out so that clogging of the filter cannot easily occur, and thus the flow-through properties of the filter are increased.

The filter material of the present invention characteristically has an average floc size index of 1.0 to 4.0. Since it is difficult to stably prepare a filter material having an average floc size index of less than 1.0, the minimum average floc size index is preferably 1.0 or more, more preferably 2.3 or more, still more preferably 2.6 or more, particularly preferably 2.7 or more, even further preferably 2.8 or more. If the average floc size index is more than 4.0, the cell-containing liquid will not uniformly flow through the filter material and thus sufficient cell separation properties cannot be obtained; in addition, a decrease in effective flow-through area and clogging are more likely to occur, thereby reducing throughput rate. Thus, the maximum average floc size index is preferably 4.0 or less, more preferably 3.4 or less, still more preferably 3.1 or less.

In the present invention, a floc size index ratio of around 1 means that there is no orientation, while the other values mean that there is a flow in a direction with a higher index. If there is an orientation in the filter material, the cell-containing liquid flows along the direction of the filter material, causing flowing on one side. Therefore, the cell separation properties of the filter are reduced as the entire surface of the filter material is not effectively used. Further, the concentrated flow of cell-containing liquid on a portion of the filter material causes clogging, thereby reducing the flow-through rate of the filter. On the other hand, if there is no orientation in the filter material, the cell-containing liquid flows uniformly through the filter material. Therefore, the cell separation properties of the filter are increased as the entire surface of the filter material is effectively used. Further, the flow of cell-containing liquid spreads out so that clogging of the filter cannot easily occur, and thus the flow-through properties of the filter are increased.

The filter material of the present invention characteristically has a floc size index ratio of 0.78 to 1.02. If the floc size index ratio is more than 1.02, since there is an orientation in the cross direction of the filter material and the flow of cell-containing liquid will concentrate in the cross direction, a decrease in flow-through area and clogging are more likely to occur and thus sufficient cell separation properties cannot be obtained; in addition, since a decrease in flow-through area and clogging are more likely to occur, throughput rate is reduced. Thus, the maximum floc size index ratio is preferably 1.02. Conversely, if the floc size index ratio is less than 0.78, since there is an orientation in the machine direction of the filter material and the flow of cell-containing liquid will concentrate in the machine direction, a decrease in flow-through area and clogging are more likely to occur and thus sufficient cell separation properties cannot be obtained; in addition, since a decrease in flow-through area and clogging are more likely to occur, throughput rate is reduced. Thus, the minimum floc size index ratio is preferably 0.78, more preferably 0.87 or more, still more preferably 0.90 or more, particularly preferably 0.98 or more.

The filter material of the present invention characteristically has a thickness of 0.10 to 0.60 mm. The minimum thickness is 0.10 mm or more, preferably 0.12 mm or more, still more preferably 0.14 mm or more. The filter material having a thickness of less than 0.10 is not preferred because it tends to be difficult to stably prepare such a filter material. Conversely, the maximum thickness is 0.60 mm or less, preferably 0.55 mm or less, still more preferably 0.50 mm or less. The filter material having a thickness of more than 0.60 mm is not preferred because such a filter material tends to have a non-uniform basis weight.

The term "thickness" as used herein refers to a value determined by the following procedure. Three filter materials are prepared, and the thickness of each filter material is measured. The thickness is measured at four points using a thickness meter (PEACOCK MODEL H, Ozaki MFG. Co., Ltd.), and the average of the three filter materials is defined as the thickness of the filter materials.

Since a filter material with a larger thickness has a non-uniform basis weight as described above, the average floc size index and the floc size index ratio are each preferably calculated using the filter material having a thickness of 0.10 mm to 0.60 mm. It is more preferred to calculate an average floc size index and a floc size index ratio each corresponding to that determined for a thickness of 0.30 mm which is an intermediate value between the maximum and the minimum thicknesses. The term "average floc size index corresponding to that determined for a thickness of 0.30 mm" refers to an average floc size index calculated with a thickness of 0.30 mm from a linear regression equation between the thickness and the average floc size index. Also, the term "floc size index ratio corresponding to that determined for a thickness of 0.30 mm" refers to a floc size index ratio calculated with a thickness of 0.30 mm from a linear regression equation between the thickness and the floc size index ratio.

The average floc size index and the floc size index ratio corresponding to those determined for a thickness of 0.30 mm are also calculated as follows. First, three filter materials that are identical in terms of the type of material, fiber diameter, packing ratio, and the like and have a uniform thickness are prepared, and the average floc size index, the floc size index ratio, and the thickness of each filter material are measured. The thickness is measured at four points using a thickness meter (PEACOCK MODEL H, OZAKI MFG. CO., LTD.), and the average is defined as the thickness of the filter materials. Subsequently, two out of the three filter materials measured are superimposed on each other, and then the average floc size index, the floc size index ratio, and the thickness are measured. After the completion of the measurement of the average floc size index and the floc size index ratio for all the three combinations, linear regression equations between the thickness and the average floc size index and between the thickness and the floc size index ratio are determined, and then the average floc size index and the floc size index ratio for a thickness of 0.30 mm are determined from these equations. When the necessary number of filter materials for the measurement cannot be obtained from a single filter, filter materials from identical filters may be combined and measured.

The filter material of the present invention characteristically has an average floc size index corresponding to that determined for a thickness of 0.30 mm of 1.0 to 3.0. Since it is difficult to stably prepare a filter material having an average floc size index corresponding to that determined for a thickness of 0.30 mm of less than 1.0, the minimum average floc size index corresponding to that determined for a thickness of 0.30 mm is preferably 1.0 or more, more preferably 2.4 or more. If the average floc size index corresponding to that determined for a thickness of 0.30 mm is more than 3.0, the structure of the filter material is not uniform in the filtration surface direction and the cell-containing liquid will not uniformly flow through the filter material, and thus sufficient cell separation properties cannot be obtained; in addition, a decrease in effective flow-through area and clogging are more likely to occur, thereby reducing throughput rate. Thus, the maximum average floc size index corresponding to that determined for a thickness of 0.30 mm is preferably 3.0 or less, more preferably 2.8 or less, still more preferably 2.7 or less.

The filter material of the present invention characteristically has a floc size index ratio corresponding to that determined for a thickness of 0.30 mm of 0.84 to 1.02. If the floc size index ratio corresponding to that determined for a thickness of 0.30 mm is more than 1.02, since there is an orientation in the cross direction of the filter material and the flow of cell-containing liquid will concentrate in the cross direction, a decrease in effective flow-through area and clogging are more likely to occur and thus sufficient cell separation properties cannot be obtained; in addition, since a decrease in effective flow-through area and clogging are more likely to occur, throughput rate is reduced. Thus, the maximum floc size index ratio corresponding to that determined for a thickness of 0.30 mm is preferably 1.02. Conversely, if the floc size index ratio corresponding to that determined for a thickness of 0.30 mm is less than 0.84, since there is an orientation in the machine direction of the filter material and the flow of cell-containing liquid will concentrate in the machine direction, a decrease in effective flow-through area and clogging are more likely to occur and thus sufficient cell separation properties cannot be obtained; in addition, since a decrease in effective flow-through area and clogging are more likely to occur, throughput rate is reduced. Thus, the minimum floc size index ratio corresponding to that determined for a thickness of 0.30 mm is preferably 0.84 or more, more preferably 0.85 or more, still more preferably 0.90 or more, particularly preferably 0.98 or more.

The shape of the filter material of the present invention is desirably such that the filter material has a large surface area, in view of frequency of contact with the cell-containing liquid. Examples include fibrous structures such as woven fabrics, nonwoven fabrics, fibers, and cotton. In particular, woven fabrics or nonwoven fabrics are preferred in view of adsorption of cells and workability as separation materials, and nonwoven fabrics are most preferred among these because they can make multipoint contact with cells. The term "nonwoven fabric" refers to a fabric material in which fibers or aggregates of fibers are bonded together chemically, thermally, or mechanically without knitting or weaving. Mechanically bonded fibers include fibers that maintain a certain form due to friction or entanglement with each other resulting from contact between the fibers.

The filter material includes any filter support material as long as it is less likely to cause damage to cells. Examples include polyesters, polyolefins, polyacrylonitrile, polyamides, polystyrene, polyalkyl(meth)acrylates, polyvinyl chloride, polychloroprene, polyurethane, polyvinyl alcohol, polyvinyl acetate, polysulfone, polyether sulfone, polybutadiene, butadiene-acrylonitrile copolymers, styrene-butadiene copolymers, ethylene-vinyl alcohol copolymers, cellulose diacetate, and ethyl cellulose. Polyesters or polyolefins are preferred, and polyesters are particularly preferred. Further, among polyesters, polyethylene terephthalate or polybutylene terephthalate is preferred, and polyethylene terephthalate is particularly preferred.

The nonwoven fabric can be produced by either wet methods or dry methods. In particular, a meltblown method, a flash spinning method, a sheet-forming method, and the like are preferred because they provide ultrafine fibers. An example of a meltblown method is described below as a method for producing the nonwoven fabric.

A thermoplastic resin melted in an extruder is spun from a meltblown die by a high-temperature high-speed airflow, and the resin extruded into fibers is accumulated on a conveyor so that the fibers are entangled and fused together, whereby a nonwoven fabric of self-bonded ultrafine fibers can be obtained without any binder. Here, the nonwoven fabric can be controlled in terms of fiber diameter, basis weight, fiber orientation, and fiber dispersibility by adjusting the resin viscosity, melting temperature, amount of discharge, hot air temperature, wind pressure, DCD (distance between the surface of the spinnerets and the conveyor), or the like. Moreover, the thickness and the average pore size of the nonwoven fabric can be controlled by thermal pressing, tentering, or the like.

The filter material of the present invention characteristically has an average fiber diameter of 0.3 to 5.0 μm. The minimum average fiber diameter is 0.3 μm or more, more preferably 0.4 μm or more, still more preferably 0.5 μm or more, especially preferably 1.0 μm or more, particularly preferably 1.2 or more. The filter material having an average fiber diameter of less than 0.3 μm is not preferred because it tends to be difficult to stably prepare such a filter material, and the viscosity resistance of the cell-containing liquid also tends to be excessively increased. Conversely, the maximum average fiber diameter is 5.0 μm or less, preferably 4.0 μm or less, more preferably 3.0 μm or less, still more preferably 2.0 μm or less. The filter material having an average fiber diameter of more than 5.0 μm is not preferred because such a filter material shows low cell separation properties. The viscosity resistance of the cell-containing liquid can be evaluated based on, for example, the pressure loss of the filter, and the cell separation properties can be evaluated based on, for example, cell separation rate.

The term "average fiber diameter" as used herein refers to a value determined by the following procedure. Specifically, a portion of the filter material is sampled, randomly selected 100 or more fibers are measured for diameter based on a scanning electron micrograph, and then the measured values are number averaged.

The minimum average pore size of the filter material of the present invention is preferably 4.0 µm or more, more preferably 4.5 µm or more, still more preferably 5.0 µm or more. The filter material having an average pore size of less than 4.0 µm is not preferred because such a filter material tends to have reduced flow-through properties. Conversely, the maximum average pore size is preferably 30.0 µm or less, more preferably 20.0 µm or less, still more preferably 15.0 µm or less, particularly preferably 10.0 µm or less. The filter material having an average pore size of more than 30.0 µm is not preferred because such a filter material tends to have reduced cell separation properties.

The flow-through properties can be evaluated based on, for example, filtration time. The term "average pore size of the filter material" as used herein refers to a mean flow pore size determined by Perm Porometer (PMI).

The minimum bulk density of the filter material of the present invention is preferably 0.05 g/cm$^3$ or more, more preferably 0.06 g/cm$^3$ or more, still more preferably 0.07 g/cm$^3$ or more. The filter material having a bulk density of less than 0.05 g/cm$^3$ is not preferred because cells can easily leak through such a filter material and thus cell separation properties are reduced. Conversely, the maximum bulk density is preferably 0.40 g/cm$^3$ or less, more preferably 0.35 g/cm$^3$ or less, still more preferably 0.30 g/cm$^3$ or less. The filter material having a bulk density of more than 0.40 g/cm$^3$ is not preferred because such a filter material tends to be dense in terms of inter-fiber distance and have reduced blood flow-through properties. The term "bulk density" as used herein refers to a value of the weight per cubic centimeter of the filter material.

The surface of the filter material of the present invention is preferably modified by, for example, graft polymerization, polymer coating, chemical treatment with alkali, acid, or the like, or plasma treatment. Among these, polymer coating is preferred because it is a simple and excellent method for modifying the surface of a polymer material so as to have a desired structure.

The filter material of the present invention preferably contains a hydrophilic polymer on at least the surface thereof. The polymer to be used for coating the surface may be any hydrophilic polymer as long as it does not impose a particularly large load on cells. Particularly preferred are copolymers of hydrophilic functional group-containing monomers such as hydroxyethyl(meth)acrylate with dimethylaminoethyl (meth)acrylate or diethylaminoethyl(meth)acrylate each of which has a basic functional group, and polyvinylpyrrolidone because in addition to hydrophilizing the material surface to improve wettability of the filter material, these polymers introduce charged functional groups to improve cell capture performance.

Any of various methods can be used to coat the filter support material with the polymer as long as they do not significantly block the pores of the filter support material and can uniformly coat a certain range of the surface of the filter support material. Examples include a method in which the filter support material is immersed in a solution of the polymer, a method in which a solution of the polymer is sprayed to the filter support material, and a method in which a solution of the polymer is applied or transferred to the filter support material using a gravure roll or the like. Among these, the method in which the filter support material is immersed in a solution of the polymer is preferred because of its excellent continuous productivity and low cost.

Any solvent may be used to dissolve the polymer as long as it does not significantly dissolve the filter support material. Examples include amides such as N,N-dimethylformamide and N,N-dimethylacetamide, sulfoxides such as dimethyl sulfoxide, alcohols such as methanol, ethanol, propanol, and butanol, ketones such as acetone and methyl ethyl ketone, esters such as methyl acetate and ethyl acetate, hydrocarbons such as toluene and cyclohexane, halogenated hydrocarbons such as chloroform and dichloromethane, water, and a soluble range of mixtures of two or more of the above solvents. Alcohols such as methanol, ethanol, propanol, and butanol are preferred, with methanol or ethanol being particularly preferred.

The filter of the present invention is characterized as a filter provided with an inlet and an outlet for a liquid and including at least one filter material having an average fiber diameter of 0.3 to 30 µm and a basis weight of 10 to 100 g/m$^2$, wherein at least one of the at least one filter material is a filter material having an average floc size index of 1.0 to 4.0.

The minimum average fiber diameter of the filter material included in the filter is 0.3 µm or more, more preferably 0.4 µm or more, still more preferably 0.5 µm or more, especially preferably 1.0 µm or more, particularly preferably 1.2 µm or more. The filter material having an average fiber diameter of less than 0.3 µm is not preferred because it tends to be difficult to stably prepare such a filter material, and the viscosity resistance of the cell-containing liquid also tends to be excessively increased. Conversely, the maximum average fiber diameter is 30 µm or less, preferably 25 µm or less, more preferably 20 µm or less, particularly preferably 15 µm or less. The filter material having an average fiber diameter of more than 30 µm is not preferred because such a filter material tends to have low cell separation properties.

The minimum basis weight of the filter material included in the filter is 10 g/m$^2$ or more, preferably 20 g/m$^2$ or more, more preferably 30 g/m$^2$ or more. The filter material having a basis weight of less than 10 g/m$^2$ is not preferred because it is difficult to stably prepare such a filter material. Conversely, the maximum basis weight is 100 g/m$^2$ or less, preferably 90 g/m$^2$ or less, more preferably 80 g/m$^2$ or less, still more preferably 70 g/m$^2$ or less. The filter material having a basis weight of more than 100 g/m$^2$ is not preferred because larger surface irregularities can be easily formed and it is thus difficult to prepare a uniform filter material.

The expression "at least one of the at least one filter material" as used herein means that the at least one filter material includes one or more filter materials in which anyone of the following parameters satisfies a specific numerical range defined herein: average floc size index, floc size index ratio, average floc size index corresponding to that determined for a thickness of 0.30 mm, and floc size index ratio corresponding to that determined for a thickness of 0.30 mm. More specifically, the at least one filter material includes such filter material(s) in an amount of 1% or more, preferably 5% or more, more preferably 6.2% or more, still more preferably 10% or more, especially preferably 50% or more, even further preferably 75%, particularly preferably 81% or more, most preferably 85% or more of the total filter material.

The minimum average floc size index of the at least one of the at least one filter material included in the filter is 1.0 or more, more preferably 2.3 or more, still more preferably 2.6 or more, particularly preferably 2.7 or more, even further preferably 2.8 or more. If each of the at least one filter material has an average floc size index of less than 1.0, such a filter material is not preferred because it is difficult to stably prepare. Conversely, the maximum average floc size index is 4.0 or less, more preferably 3.4 or less, still more preferably 3.1 or less. If each of the at least one filter material has an average floc size index of more than 4.0, such a filter material is not preferred because the cell-containing liquid will not uniformly flow through the filter and thus sufficient cell separation properties cannot be obtained; in addition, a decrease in effective flow-through area and clogging are more likely to occur, thereby reducing throughput rate.

The filter housing may be in any form such as a sphere, container, cassette, bag, tube, or column. For example, it is preferably a transparent or translucent cylindrical housing having a capacity of about 0.1 to 1000 mL and a diameter of about 0.1 to 15 cm, or a quadrangular prism form with a square or rectangular base with a side length of about 0.1 to 20 cm and having a thickness of about 0.1 to 5 cm, or the like.

The filter of the present invention is characterized in that at least one of the at least one filter material is a filter material having a floc size index ratio of 0.78 to 1.02.

If each of the at least one filter material has a floc size index ratio of more than 1.02, since there is an orientation in the cross direction of the filter and the flow of cell-containing liquid will concentrate in the cross direction, a decrease in flow-through area and clogging are more likely to occur and thus sufficient cell separation properties cannot be obtained; in addition, since a decrease in flow-through area and clogging are more likely to occur, throughput rate is reduced. Thus, the maximum floc size index ratio is preferably 1.02. Conversely, if each of the at least one filter material has a floc size index ratio of less than 0.78, since there is an orientation in the machine direction of the filter and the flow of cell-containing liquid will concentrate in the machine direction, a decrease in flow-through area and clogging are more likely to occur and thus sufficient cell separation properties cannot be obtained; in addition, since a decrease in flow-through area and clogging are more likely to occur, throughput rate is reduced. Thus, the minimum floc size index ratio is preferably 0.78, more preferably 0.87 or more.

The filter of the present invention is characterized in that at least one of the at least one filter material is a filter material having an average floc size index corresponding to that determined for a thickness of 0.30 mm of 1.0 to 3.0.

If each of the at least one filter material has an average floc size index corresponding to that determined for a thickness of 0.30 mm of less of 1.0, it is difficult to stably prepare such a filter material. For this reason, the minimum average floc size index corresponding to that determined for a thickness of 0.30 mm of the at least one of the at least one filter material included in the filter is preferably 1.0 or more, more preferably 2.4 or more.

Conversely, if each of the at least one filter material has an average floc size index corresponding to that determined for a thickness of 0.30 mm of more than 3.0, the structure of the filter is not uniform in the filtration surface direction and the cell-containing liquid will not uniformly flow through the filter, and thus sufficient cell separation properties cannot be obtained; in addition, a decrease in effective flow-through area and clogging are more likely to occur, thereby reducing throughput rate. Thus, the maximum average floc size index corresponding to that determined for a thickness of 0.30 mm is preferably 3.0 or less, more preferably 2.8 or less, still more preferably 2.7 or less.

The filter of the present invention is characterized in that at least one of the at least one filter material is a filter material having a floc size index ratio corresponding to that determined for a thickness of 0.30 mm of 0.84 to 1.02.

If each of the at least one filter material has a floc size index ratio corresponding to that determined for a thickness of 0.30 mm of more than 1.02, since there is an orientation in the cross direction of the filter and the flow of cell-containing liquid will concentrate in the cross direction, a decrease in effective flow-through area and clogging are more likely to occur and thus sufficient cell separation properties cannot be obtained; in addition, since a decrease in effective flow-through area and clogging are more likely to occur, throughput rate is reduced. Thus, the maximum floc size index ratio corresponding to that determined for a thickness of 0.30 mm is preferably 1.02.

Conversely, if each of the at least one filter material has a floc size index ratio corresponding to that determined for a thickness of 0.30 mm of less than 0.84, since there is an orientation in the machine direction of the filter and the flow of cell-containing liquid will concentrate in the machine direction, a decrease in effective flow-through area and clogging are more likely to occur and thus sufficient cell separation properties cannot be obtained; in addition, since a decrease in effective flow-through area and clogging are more likely to occur, throughput rate is reduced. Thus, the minimum floc size index ratio corresponding to that determined for a thickness of 0.30 mm is preferably 0.84 or more, more preferably 0.85 or more, still more preferably 0.90 or more, particularly preferably 0.98 or more.

In the filter of the present invention, the at least one filter material may be stacked in a liquid flow direction and packed in a housing. The minimum number of filter materials stacked is one, but in view of cell separation properties, the minimum number is preferably 5 or more, more preferably 10. Conversely, the maximum number of filter materials stacked is preferably 100 or less, more preferably 70 or less, still more preferably 50 or less. If the number of filter materials stacked is more than 100, the problem of reduced flow-through properties will occur.

The filter of the present invention may further include a different type of filter material on the inlet side and/or the outlet side of the filter. For example, effects such as further improved blood flow-through properties can be expected when a filter material having a larger average fiber diameter than the main filter material is placed on the inlet side.

In the filter of the present invention, a filter material having a large average fiber diameter may be placed on the inlet side of the filter while a filter material having a small average fiber diameter is placed on the outlet side of the filter. In such a case, the filter material on the outlet side is referred to as a first filter material, and the filter material on the inlet side is referred to as a second filter material.

Further improved blood flow-through properties can be obtained when the first filter material has an average fiber diameter of 0.3 to 5.0 μm and the second filter material having an average fiber diameter that is 1.0 to 10.0 μm and is larger than the first filter material is placed on the inlet side of the first filter material.

The minimum average fiber diameter of the second filter material is 1.0 μm or more, more preferably 1.2 μm or more, still more preferably 1.5 μm or more. The second filter material having an average fiber diameter of less than 1.0 μm is not preferred because the degree of improvement in flow-through properties is low. Conversely, the maximum average fiber diameter is 10.0 μm or less, more preferably 8.0 μm or less, more preferably 5.0 μm or less, still more preferably 3.0 μm or less. The second filter material having an average fiber diameter of more than 10.0 μm is not preferred because the degree of improvement in flow-through properties is low.

The filter of the present invention may include a pre-filter material for removing microscopic aggregates on the inlet side of the filter. Since cell-containing liquids often contain microscopic aggregates, it is preferred to remove the microscopic aggregates using a pre-filter. The pre-filter is preferably, for example, an aggregate of fibers having an average fiber diameter of 3 to 50 μm, a continuous porous body with pores having an average pore size of 20 to 200 μm, or the like.

The filter system of the present invention characteristically includes the filter; a blood collection bag connected to the inlet side of the filter, and at least one blood bag connected to the outlet side of the filter. The blood collection bag refers to, for example, a bag to which a blood collection tube with a blood collection needle is connected and into which an anticoagulant such as acid citrate dextrose (ACD) or citrate phosphate dextrose (CPD) is injected. Blood collection bags commonly used in blood collection can also be used. Moreover, the blood bag refers to a bag for preserving whole blood, concentrated red cells, platelet-concentrated plasma, plasma, or the like. Commonly used blood bags can be used.

EXAMPLES

The present invention is described in further detail below with reference to examples, but the present invention is not limited to these examples.

Example 1

<Preparation of Nonwoven Fabric>
The following polyethylene terephthalate (hereinafter abbreviated to "PET") nonwoven fabrics produced by the meltblown method were used.

Pre-filter material: PET nonwoven fabric having an average fiber diameter of 15 μm and a basis weight of 30 g/m$^2$ Second filter material: PET nonwoven fabric having an average fiber diameter of 1.8 μm, a basis weight of 70 g/m$^2$, an average pore size of 7.7 μm, a bulk density of 0.20 g/cm$^3$, a thickness of 0.35 mm, an average floc size index of 2.6, a floc size index ratio of 0.98, an average floc size index corresponding to that determined for a thickness of 0.30 mm of 2.7, and a floc size index ratio corresponding to that determined for a thickness of 0.30 mm of 0.98

First filter material: PET nonwoven fabric having an average fiber diameter of 1.4 μm, a basis weight of 40 g/m$^2$, an average pore size of 4.9 μm, a bulk density of 0.18 g/cm$^3$, a thickness of 0.22 mm, an average floc size index of 3.1, a floc size index ratio of 0.98, an average floc size index corresponding to that determined for a thickness of 0.30 mm of 2.8, and a floc size index ratio corresponding to that determined for a thickness of 0.30 mm of 0.98

<Step of Preparing Coating Solution>
2-Hydroxyethyl methacrylate and 2-dimethylaminoethyl methacrylate were added to special grade ethanol at concentrations of 0.95 mol/L and 0.05 mol/L, respectively, to give a total amount of 300 mL.

2,2'-Azobis(2,4-dimethylvaleronitrile) (V-65) as an initiator was added to the mixture at a concentration of 0.005 mol/L, and polymerization was carried out in a nitrogen atmosphere at 45° C. for 15 hours. Then, the reaction mixture was poured into excess n-hexane to precipitate and recover a polymer. The obtained polymer was re-dissolved in ethanol and the solution was poured into n-hexane to precipitate the polymer, which was then dried at 75° C. for four hours to give a copolymer of 2-hydroxyethyl methacrylate and N,N-dimethylaminoethyl methacrylate (hereinafter abbreviated to "HEDM"). HEDM was dissolved in ethanol to a concentration of 1.0 g/L to prepare a HEDM coating solution.

<Step of Coating Nonwoven Fabric>
The second filter material and the first filter material were immersed in the HEDM coating solution at 20° C. for five minutes and then placed in a stainless-steel basket and dried at 50° C. for 1.5 hours. Subsequently, the nonwoven fabrics were washed with water and then placed in a stainless-steel basket and dried at 50° C. for three hours.

<Step of Preparing Nonwoven Fabric Disk>
A punch was used to punch out each nonwoven fabric in the shape of a circle having a diameter of 18 mm to prepare a disk-shaped pre-filter material, second filter material, and first filter material.

<Step of Preparing Filter>
A filter was prepared by inserting the following filters into a cylindrical housing having an inner diameter of 18 mm in the stated order from the inlet side to the outlet side: 6 pre-filter materials, 2 second filter materials (accounting for 6.25% of the total filter material), and 24 first filter materials (accounting for 75% of the total filter material). The inlet of the filter and a blood storage container were connected to each other via a 60 cm-long vinyl chloride tube (outer diameter 5 mm, inner diameter 3 mm), and the tube was closed with a clamp.

<Evaluation of Filter Properties>
A blood sample was prepared by adding 10% of a 5% aqueous solution of trisodium citrate as an anticoagulant to bovine blood. After the blood sample was brought to 28° C. in a temperature-controlled bath, the blood sample (24 mL) was placed in a blood storage container and filtered by gravity at a head of 60 cm to collect the filtered blood (22 mL) in a receptacle. The time from the start of filtration until the blood storage container became empty was defined as the filtration time. The leukocyte concentration before the filtration, and the erythrocyte concentration and the platelet concentration before and after the filtration were measured using a blood cell counter (K-4500 available from Sysmex Corporation), and the leukocyte concentration after the filtration was measured by flow cytometry using Leuco-COUNT kit and FACSCalibur (both available from Becton, Dickinson and Company).

The leukocyte separation performance (−Log), the erythrocyte recovery rate (%), and the platelet separation rate (%) were determined by the following formulas:

$$\text{leukocyte separation performance} = -\text{Log}(b/a), \text{ erythrocyte recovery rate} = d/c \times 100(\%), \text{ and platelet separation rate} = (e-f)/e \times 100(\%),$$

where a=leukocyte concentration in blood before filtration, b=leukocyte concentration in blood after filtration, c=erythrocyte concentration in blood before filtration, d=erythrocyte concentration in blood after filtration, e=platelet concentration in blood before filtration, and f=platelet concentration in blood after filtration. Table 1 shows the results.

Example 2

A filter was prepared in the same manner as in Example 1, except that the first filter material was a PET nonwoven fabric having an average fiber diameter of 1.3 μm, a basis weight of 40 g/m$^2$, an average pore size of 6.8 μm, a bulk density of 0.13 g/cm$^3$, a thickness of 0.30 mm, an average floc size index of 2.7, a floc size index ratio of 1.02, an average floc size index corresponding to that determined for a thickness of 0.30 mm of 2.7, and a floc size index ratio corresponding to that determined for a thickness of 0.30 mm of 1.02, and 24 first filter materials were used. The prepared filter was evaluated as in Example 1. Table 1 shows the results.

Example 3

A filter was prepared in the same manner as in Example 1, except that the first filter material was a PET nonwoven fabric having an average fiber diameter of 1.3 μm, a basis weight of 40 g/m$^2$, an average pore size of 7.0 μm, a bulk density of 0.11 g/cm$^3$, a thickness of 0.35 mm, an average floc size index of 2.7, a floc size index ratio of 0.99, an average floc size index corresponding to that determined for a thickness of 0.30 mm of 2.7, and a floc size index ratio corresponding to that determined for a thickness of 0.30 mm of 0.99, and 24 first filter materials were used. The prepared filter was evaluated as in Example 1. Table 1 shows the results.

Example 4

A filter was prepared in the same manner as in Example 1, except that the first filter material was a PET nonwoven fabric having an average fiber diameter of 1.3 μm, a basis weight of 40 g/m$^2$, an average pore size of 6.0 μm, a bulk density of 0.10 g/cm$^3$, a thickness of 0.40 mm, an average floc size index of 2.8, a floc size index ratio of 0.98, an average floc size index corresponding to that determined for a thickness of 0.30 mm of 3.0, and a floc size index ratio corresponding to that determined for a thickness of 0.30 mm of 0.98, and 24 first filter materials were used. The prepared filter was evaluated as in Example 1. Table 1 shows the results.

Example 5

A filter was prepared in the same manner as in Example 1, except that the first filter material was a PET nonwoven fabric having an average fiber diameter of 1.5 μm, a basis weight of 40 g/m$^2$, an average pore size of 5.2 μm, a bulk density of 0.11 g/cm$^3$, a thickness of 0.38 mm, an average floc size index of 2.3, a floc size index ratio of 0.87, an average floc size index corresponding to that determined for a thickness of 0.30 mm of 2.4, and a floc size index ratio corresponding to that determined for a thickness of 0.30 mm of 0.85, and 24 first filter materials were used. The prepared filter was evaluated as in Example 1. Table 1 shows the results.

Example 6

A filter was prepared in the same manner as in Example 1, except that the first filter material was a PET nonwoven fabric having an average fiber diameter of 1.5 μm, a basis weight of 40 g/m$^2$, an average pore size of 4.7 μm, a bulk density of 0.08 g/cm$^3$, a thickness of 0.55 mm, an average floc size index of 2.6, a floc size index ratio of 0.90, an average floc size index corresponding to that determined for a thickness of 0.30 mm of 2.7, and a floc size index ratio corresponding to that determined for a thickness of 0.30 mm of 0.90, and 24 first filter materials were used. The prepared filter was evaluated as in Example 1. Table 1 shows the results.

Example 7

A filter was prepared in the same manner as in Example 1, except that the first filter material was a PET nonwoven fabric having an average fiber diameter of 1.2 μm, a basis weight of 40 g/m$^2$, an average pore size of 5.1 μm, a bulk density of 0.19 g/cm$^3$, a thickness of 0.21 mm, an average floc size index of 3.4, a floc size index ratio of 0.78, an average floc size index corresponding to that determined for a thickness of 0.30 mm of 3.0, and a floc size index ratio corresponding to that determined for a thickness of 0.30 mm of 0.84, and 24 first filter materials were used. The prepared filter was evaluated as in Example 1. Table 1 shows the results.

Comparative Example 1

A filter was prepared in the same manner as in Example 1, except that the first filter material was a PET nonwoven fabric having an average fiber diameter of 1.3 μm, a basis weight of 40 g/m$^2$, an average pore size of 4.9 μm, a bulk density of 0.20 g/cm$^3$, a thickness of 0.20 mm, an average floc size index of 4.1, a floc size index ratio of 1.13, an average floc size index corresponding to that determined for a thickness of 0.30 mm of 3.4, and a floc size index ratio corresponding to that determined for a thickness of 0.30 mm of 1.11, and 24 first filter materials were used.

Comparative Example 2

A filter was prepared in the same manner as in Example 1, except that the first filter material was a PET nonwoven fabric having an average fiber diameter of 1.1 μm, a basis weight of 30 g/m$^2$, an average pore size of 5.1 μm, a bulk density of 0.20 g/cm$^3$, a thickness of 0.15 mm, an average floc size index of 4.6, a floc size index ratio of 1.03, an average floc size index corresponding to that determined for a thickness of 0.30 mm of 4.4, and a floc size index ratio corresponding to that determined for a thickness of 0.30 mm of 1.02, and 32 first filter materials were used.

Comparative Example 3

A filter was prepared in the same manner as in Example 1, except that the first filter material was a PET nonwoven fabric having an average fiber diameter of 1.3 μm, a basis weight of 50 g/m$^2$, an average pore size of 4.7 μm, a bulk density of 0.21 g/cm$^3$, a thickness of 0.23 mm, an average floc size index of 4.3, a floc size index ratio of 0.97, an average floc size index corresponding to that determined for a thickness of 0.30 mm of 3.9, and a floc size index ratio corresponding to that determined for a thickness of 0.30 mm of 0.98, and 19 first filter materials were used.

TABLE 1

| | Average fiber diameter (μm) | Basis weight (g/m²) | Average pore size (μm) | Bulk density (g/cm³) | Thickness (mm) | Average floc size index | Floc size index ratio | Average floc size index (corresponding to that determined for 0.30 mm) | Floc size index ratio (corresponding to that determined for 0.30 mm) | Leukocyte separation performance (-Log) | Erythrocyte recovery rate (%) | Platelet separation rate (%) | Filtration time (min) |
|---|---|---|---|---|---|---|---|---|---|---|---|---|---|
| Example 1 | 1.4 | 40 | 4.9 | 0.18 | 0.22 | 3.1 | 0.98 | 2.8 | 0.93 | 5.41 or more | 100 | 100 | 22.4 |
| Example 2 | 1.3 | 40 | 6.8 | 0.13 | 0.30 | 2.7 | 1.02 | 2.7 | 1.02 | 5.51 or more | 100 | 100 | 18.6 |
| Example 3 | 1.3 | 40 | 7.0 | 0.11 | 0.35 | 2.7 | 0.99 | 2.7 | 0.99 | 5.51 or more | 100 | 100 | 18.1 |
| Example 4 | 1.3 | 40 | 6.0 | 0.10 | 0.40 | 2.8 | 0.98 | 3.0 | 0.98 | 5.51 or more | 100 | 100 | 16.9 |
| Example 5 | 1.5 | 40 | 5.2 | 0.11 | 0.38 | 2.3 | 0.87 | 2.4 | 0.85 | 5.37 | 100 | 100 | 33.1 |
| Example 6 | 1.5 | 40 | 4.7 | 0.08 | 0.55 | 2.6 | 0.90 | 2.7 | 0.90 | 5.37 | 100 | 100 | 29.8 |
| Example 7 | 1.2 | 40 | 5.1 | 0.19 | 0.21 | 3.4 | 0.78 | 3.0 | 0.84 | 4.76 | 100 | 100 | 23.6 |
| Comparative Example 1 | 1.3 | 40 | 4.9 | 0.20 | 0.20 | 4.1 | 1.13 | 3.4 | 1.11 | 3.66 | 100 | 99 | 23.6 |
| Comparative Example 2 | 1.1 | 30 | 5.1 | 0.20 | 0.15 | 4.6 | 1.03 | 4.4 | 1.02 | 3.54 | 100 | 100 | 37.5 |
| Comparative Example 3 | 1.3 | 50 | 4.7 | 0.21 | 0.23 | 4.3 | 0.97 | 3.9 | 0.98 | 3.19 | 100 | 86 | 16.9 |

The results in Table 1 show that the filter materials each having a low average floc size index and a floc size index ratio close to 1.00 simultaneously exhibited high cell separation properties and high flow-through properties.

Example 8

Evaluation of Filtration of Large Amount of Blood

<Step of Preparing Nonwoven Fabric>

The following PET nonwoven fabrics produced by the meltblown method were used.

Pre-filter material: PET nonwoven fabric having an average fiber diameter of 15 μm and a basis weight of 30 g/m²

Second filter material: PET nonwoven fabric having an average fiber diameter of 1.8 μm, a basis weight of 70 g/m², an average pore size of 7.7 μm, a bulk density of 0.20 g/cm³, a thickness of 0.35 mm, an average floc size index of 2.6, a floc size index ratio of 0.98, an average floc size index corresponding to that determined for a thickness of 0.30 mm of 2.7, and a floc size index ratio corresponding to that determined for a thickness of 0.30 mm of 0.98.

First filter material: PET nonwoven fabric having an average fiber diameter of 1.4 μm, a basis weight of 40 g/m², an average pore size of 4.9 μm, a bulk density of 0.18 g/cm³, a thickness of 0.22 mm, an average floc size index of 3.1, a floc size index ratio of 0.98, an average floc size index corresponding to that determined for a thickness of 0.30 mm of 2.8, and a floc size index ratio corresponding to that determined for a thickness of 0.30 mm of 0.98.

<Step of Coating Nonwoven Fabric>

The second filter material and the first filter material were immersed in the HEDM coating solution at 20° C. for five minutes and then placed in a stainless-steel basket and dried at 50° C. for 1.5 hours. Subsequently, the nonwoven fabrics were washed with water and then placed in a stainless-steel basket and dried at 50° C. for three hours.

<Step of Preparing Nonwoven Fabric Disk>

A punch was used to punch out each nonwoven fabric in the shape of a square of 7.2 cm×7.2 cm to prepare a disk-shaped pre-filter material, second filter material, and first filter material.

<Step of Preparing Filter>

A filter was prepared by inserting the following filters into a 7.2 cm×7.2 cm square housing in the stated order from the inlet side to the outlet side: 6 pre-filter materials, 2 second filter materials, and 32 first filter materials. The inlet of the filter and a blood bag were connected to each other via a 60 cm-long vinyl chloride tube (outer diameter 5 mm, inner diameter 3 mm), and the tube was closed with a clamp.

<Evaluation of Filter Properties>

A blood sample was prepared by adding 10% of a 5% aqueous solution of trisodium citrate as an anticoagulant to bovine whole blood. After the blood sample (456 mL) was placed in the blood bag and brought to 28° C. in a temperature-controlled bath, the blood sample was filtered by gravity at a head of 60 cm using the above filter. As a result, the leukocyte separation performance (-Log) was 5.29, the erythrocyte recovery rate was 100%, the platelet separation rate was 86.6%, and the filtration time was 14.5 minutes.

Example 9

Evaluation Using Human Blood

A filter was prepared as in Example 1, except that 32 first filter materials were used.

<Evaluation of Filter Properties>

Human whole blood (200 mL) was collected and mixed in a blood bag containing an anticoagulant CPD solution (28 mL) (a blood bag CPD available from Terumo Corporation; composition: 2.63 w/v % sodium citrate hydrate, 0.327 w/v % citrate hydrate, 2.32 w/v % glucose, 0.251 w/v % sodium dihydrogen phosphate) to prepare a blood sample. After the blood sample was brought to 28° C. in a temperature-controlled bath, the blood sample (24 mL) was placed in a blood storage container and filtered by gravity at a head of 60 cm to collect the filtered blood (22 mL) in a receptacle. As a result, the leukocyte separation performance (-Log) was 5.27, the erythrocyte recovery rate was 1000, the platelet separation rate was 100%, and the filtration time was 26.3 minutes.

The invention claimed is:

1. A filter comprising:
   an inlet and an outlet for a liquid; and
   at least two nonwoven fabrics stacked in a liquid flow direction,
   wherein
   a nonwoven fabric, of the at least two nonwoven fabrics, on an inlet side of the filter, and a nonwoven fabric, of the at least two nonwoven fabrics, on an outlet side of the filter have an average fiber diameter of from 0.3 to 5.0 μm,
   a thickness of from 0.10 to 0.60 mm,
   a basis weight of from 10 to 100 g/m², and
   an average floc size index of from 1.0 to 4.0.

2. The filter according to claim 1, wherein the nonwoven fabric on an outlet side of the filter has a floc size index ratio of from 0.78 to 1.02.

3. The filter according to claim 1, wherein the nonwoven fabric on an outlet side of the filter has an average floc size index corresponding to that determined for a thickness of from 0.30 mm of 1.0 to 3.0.

4. The filter according to claim 1, wherein the nonwoven fabric on an outlet side of the filter has a floc size index ratio of from 0.84 to 1.02 that corresponds to an average floc size index determined for a thickness of 0.30 mm.

5. The filter according to claim 1, further comprising:
   a different type of a filter material which is different from the at least two nonwoven fabrics, wherein the different type of a filter material is positioned on an inlet side, an outlet side, or both, of the filter.

6. The filter according to claim 1, wherein
   the filter comprises a first filter material positioned on an outlet side of the filter and a second filter material positioned on an inlet side of the filter, and
   an average fiber diameter of the second filter material is larger than an average fiber diameter of the first filter material.

7. The filter according to claim 1, further comprising:
   a pre-filter material configured to remove microscopic aggregates and positioned on an inlet side of the filter.

8. A filter system, comprising:
   the filter according to claim 1;
   a blood collection bag connected to an inlet side of the filter; and
   at least one blood bag connected to an outlet side of the filter.

9. The filter according to claim 1, wherein the filter comprises from 5 to 100 filter materials.

10. The filter according to claim 6, wherein the average fiber diameter of the first filter material is from 0.3 to 5.0 μm, and the average fiber diameter of the second filter material is from 1.0 to 10.0 μm.

11. The filter material according to claim 1, wherein the nonwoven fabric on an outlet side of the filter has the average fiber diameter of from 0.4 to 4.0 μm, the thickness of from 0.14 to 0.55 mm, and the average floc size index of from 2.3 to 3.4.

12. The filter material according to claim 1, wherein at least one of the nonwoven fabrics has an average pore size of from 4.0 μm to 30.0 μm.

\* \* \* \* \*